(12) United States Patent
Lesaffre

(10) Patent No.: US 7,459,159 B2
(45) Date of Patent: Dec. 2, 2008

(54) YEAST CELL WALLS FOR THE TREATMENT OR PREVENTION OF HYPERGLYCEMIA OR FOR THE STABILIZATION OF GLYCEMIA

(75) Inventor: Lucien Lesaffre, Marcq-en-Baroeul (FR)

(73) Assignee: Lesaffre et Compagnie (FR)

( * ) Notice: Subject to any disclaimer, the term of this patent is extended or adjusted under 35 U.S.C. 154(b) by 148 days.

(21) Appl. No.: 10/567,621

(22) PCT Filed: Aug. 10, 2004

(86) PCT No.: PCT/EP2004/008933

§ 371 (c)(1),
(2), (4) Date: Feb. 8, 2006

(87) PCT Pub. No.: WO2005/021015

PCT Pub. Date: Mar. 10, 2005

(65) Prior Publication Data

US 2006/0257422 A1  Nov. 16, 2006

(30) Foreign Application Priority Data

Aug. 11, 2003  (EP)  ................................. 03018222
Sep. 8, 2003  (EP)  ................................. 03020253

(51) Int. Cl.
*A61K 35/84* (2006.01)

(52) U.S. Cl. ................................. 424/195.16

(58) Field of Classification Search ....................... None
See application file for complete search history.

(56) References Cited

U.S. PATENT DOCUMENTS 4,962,094 A * 10/1990 Jamas et al. .................. 514/54
2004/0151738 A1 * 8/2004 Oriol et al. ............. 424/195.16

FOREIGN PATENT DOCUMENTS

| DE | 44 13 023 A | 10/1995 |
| DE | 198 35 767 A | 2/2000 |
| EP | 1 094 117 A | 4/2001 |
| FR | 2 825 004 A | 11/2002 |

OTHER PUBLICATIONS

"Hyperglycemia," Dictionary.com Unabridged (v 1.1), Random House, Inc. [online], [retrieved on Jan. 9, 2008], Retrieved from the Internet:<URL:http://dictionary.reference.com/browse/Hyperglycemia>.*
Temelkova-Kurktschiev et al., "Prevalence and atherosclerosis risk in different types of non-diabetic hyperglycemia. Is mild hyperglycemia an underestimated evil?" 2000, Exp Clin Endocrinol Diabetes; vol. 108: 93-99.*
Luna et al., "Drug-Induced Hyperglycemia," Oct. 24, 2001; JAMA, vol. 286 (16) :1945-1948.*
Wursch et al., "The role of viscous soluble fiber in the metabolic control of diabetes," Nov. 1997, Diabetes Care; vol. 20, Issue 11; pp. 1774-1780.*

* cited by examiner

*Primary Examiner*—Christopher R. Tate
(74) *Attorney, Agent, or Firm*—Lerner, David, Littenberg, Krumholz & Mentlik, LLP

(57) ABSTRACT

The invention relates to agents and preparations for the treatment or prevention of hyperglycemia, or for the stabilisation of glycemia, based on the cell walls of yeast and preparation of a corresponding therapeutic composition.

15 Claims, No Drawings

YEAST CELL WALLS FOR THE TREATMENT OR PREVENTION OF HYPERGLYCEMIA OR FOR THE STABILIZATION OF GLYCEMIA

The present invention relates to the treatment and the prevention of the hyperglycemia, and the stabilization of glycemia.

A large number of compounds have already been proposed for the prevention of hyperglycemia, for the treatment of hyperglycemia and/or for the stabilization of glycemia, in particular in the case of diabetes.

Products based on yeast, such as in particular yeast as such, yeast extract, a chromium-based glucose tolerance factor (GTF) extracted from a chromium-enriched yeast, and also a cellular preparation of brewer's yeast, have thus been proposed.

Thus, JP-A-61-167622 proposes an agent for combating diabetes based on a cellular fraction of brewer's yeast called cell wall in this document and obtained by hydrolysis of debittered brewer's yeast for at least 2 hours at a temperature of 50 to 70° C. and aqueous extraction of the water-soluble constituents. Said cellular fraction of brewer's yeast has in particular a glucan content of about 14.8%, a mannan content of about 13.9%. Said cellular fraction also has a glycogen content of about 24.9%. Glycogen or liver starch (in German: "Leberstärke") is a storage polysaccharide also present in the muscles and in particular in the liver. This glycogen is also a storage substance in yeast, used by the latter as energy source for its survival. While it is one of the main components of the cellular fraction described in this Japanese application, it does not form part of the cell wall in yeasts.

According to the present invention, it has been now been observed that it is possible to obtain yeast cell walls that are effective as agent for the prevention and treatment of hyperglycemia and having a low glycogen content, it being possible for said yeast cell walls to be obtained by a simple autolysis or enzymatic hydrolysis process.

The term "yeast cell wall" refers to the insoluble fraction of the non-chromium-enriched yeast cells which is obtained after autolysis or enzymatic hydrolysis, mainly by proteases, leading to the solubilization of at least 50%, and preferably of at least 60% by mass of the dry matter content of the whole yeast cells and preserving the structural polysaccharides of the cell wall, that is to say the β-glucans and the mannans, these mannans being in the form of mannoproteins.

This autolysis or enzymatic hydrolysis is performed so as to solubilize most of the storage sugars of the yeast cell such as glycogen and trehalose. The yeast cell walls are obtained by separating the fraction solubilized by autolysis or enzymatic hydrolysis, the latter having a duration preferably of at least 18 hours. The preferred processes for autolysis of cream yeasts are described on pages 370 to 377 in the reference manual "Yeast Technology", 2nd edition, 1991, G. Reed. and T. W. Nogodawithana, published by Van Nostrand Reinhold, New York, ISBN 0-442-31892-8. The yeast cell walls thus obtained are then typically dried by a conventional drying process, such as spray-drying or drying on rotary drums.

The yeast cell walls according to the invention are cell walls of yeasts of the genus *Saccharomyces* preferably belonging to the species *Saccharomyces cerevisiae*.

Said yeasts are preferably baker's yeasts. Baker's yeast is a yeast belonging to the species *Saccharomyces cerevisiae*, manufactured mainly with the aid of an aerobic multiplication or culture as taught in the reference manual "Yeast Technology" cited above and which has not served, before its autolysis or enzymatic hydrolysis, for any purpose, unlike, for example, brewer's yeast which is a by-product of beer manufacture and which has therefore served for the manufacture of beer before its recovery for its autolysis or enzymatic hydrolysis. This brewer's yeast was mainly multiplied under anaerobic conditions (the manufacture of beer being an anaerobic process).

The yeast cell walls according to the invention have a total cell wall glucan and mannan content (systematically expressed as equivalent mass of glycose and mannose respectively—see methods of measurement below) of at least 34.0% by mass on a dry matter basis, and a glycogen content (systematically expressed as equivalent mass of glucose—see methods of measurement below) of less than 10.0% by mass on a dry matter basis.

Preferably, the yeast cell walls according to the invention have a total glucan and mannan content of at least 40.0% by mass on a dry matter basis, preferably still of at least 45.0% by mass on a dry matter basis.

The yeast cell walls according to the invention also preferably have a glycogen content of less than 8.0% by mass on a dry matter basis, preferably still of less than 5.0% by mass on a dry matter basis and more preferably still of less than 3.0% by mass on a dry matter basis.

Usefully, the yeast cell walls according to the invention have an N×6.25 protein content of 17.0 to 35.0% by mass on a dry matter basis, preferably of 18.0 to 26.0% by mass on a dry matter basis.

Advantageously, the yeast cell walls according to the invention have a dry matter content of at least 90% by mass, preferably of at least 94% by mass and preferably still of at least 96% by mass.

In general, the total glucan and mannan content of the yeast cell wall according to the invention is less than or equal to 70%, by mass on a dry matter basis. It may in particular be less than or equal to 65% by mass on a dry matter basis. It may also be less than or equal to 55% by mass on a dry matter basis.

According to one variant of the invention, in order to completely or practically completely remove glycogen from the yeast cell wall, yeast cell walls according to the invention, obtained as described above, are suspended in an aqueous suspension, heated in an alkaline medium at between 70° C. and 100° C. for a maximum of three hours, and the fraction solubilized by this treatment is removed, the remaining non-solubilized fraction being recovered and generally dried. For example, a suspension containing about 12% of yeast cell wall dry matter content in a sodium-containing alkaline aqueous medium may be heated at 85° C. for two hours. The solubilized fraction containing all the glycogen, but also a large portion of, or even the entire content of, mannoproteins is removed by centrifugation and washing.

Such a treatment makes it possible to produce yeast cell walls according to the invention having a total glucan and mannan content of 55%. to 70% by mass on a dry matter basis, preferably of 60% to 70% by mass and preferably still of 60 to 65% by mass on a dry matter basis. Such a treatment makes it possible in particular to prepare yeast cell walls which contain less than 1.0% by mass of glycogen on a dry matter basis, and. preferably less than 0.1% by mass of glycogen on a dry matter basis. These yeast cell walls may not contain mannans.

These yeast cell walls containing a high total glucan and mannan content correspond to one embodiment of an agent according to the invention for the treatment or prevention of hyperglycemia or for the stabilization of glycemia.

They are appropriate for the preparations according to the invention for the treatment or prevention of hyperglycemia or for the stabilization of glycemia. They may, according to the invention, be used in the preparation of a therapeutic composition for the treatment or prevention of hyperglycemia or for the stabilization of glycemia.

Method for Measuring the Glycogen Content 0.5 ml of 0.25 M $Na_2CO_3$ is added to a sample of 20 mg of dry yeast cell walls, that is to say having a dry matter content of at least 90% by mass, and this mixture is kept at 95° C. for 4 hours.

The mixture is then brought to a pH of 5.2 by adding 0.3 ml of 1 M acetic acid and 1.2 ml of 0.2 M sodium acetate and by mixing the ingredients. Distilled water is added to obtain a total volume of 2 ml.

0.5 ml of the suspension thus obtained is incubated for 15 hours in the presence of an excess of *Aspergillus niger* amyloglucosidase, as marketed by the company Roche under the number Cat. No. 102 857; at 55° C.

After centrifugation, the glucose released is measured out by enzymatic assay.

The enzymatic assay of glucose is described in particular in the manual "Methods of Biochemical Analysis and Food Analysis—using Single Reagents", published by Boehringer Mannheim GmbH Biochemica, © 1989, pages 50 to 55, and is preferably carried out using the "Test-Combination D-Glucose/-Fructose", Cat. No. 139 106 from the subsidiary of the company Roche: Boehringer Mannheim GmbH/R-Biopharm GmbH at Darmstadt, Germany.

The quantity (in mg) of glucose thus assayed corresponds to the quantity of glycogen present in the sample expressed as equivalent mass of glucose.

Method for Measuring the Total Content of Glucans and Mannans

A sample of 20 mg of dry yeast cell walls, that is to say having a dry matter content of at least 90% by mass, is subjected to acid hydrolysis by mixing it with 20 ml of 2 N HCl, and the mixture is kept in a closed screw-top bottle for 4 hours at 103° C. in an incubator with stirring every 15 min.

Next, the acidic solution thus obtained is neutralized and the quantity of glucose and of mannose, respectively, in the neutralized solution is then assayed by the enzymatic route.

This enzymatic assay of glucose and mannose is also described on pages 50 to 55 of the manual cited above and is preferably carried out using the "Test-Combination" Cat. No. 139 106.

The difference is calculated between, on the one hand, the quantity of glucose (expressed in mg) assayed according to this method and the quantity of glucose (also expressed in mg) assayed for these yeast cell walls by the method for the measurement of the glycogen content above.

This difference (in mg) between the two quantities of glucose assayed corresponds to the total quantity of glucans present in the sample, this quantity being expressed as equivalent mass of glucose.

The quantity (in mg) of mannose assayed corresponds to the total quantity of mannans present in the sample, this quantity being expressed as equivalent mass of mannose.

The present invention relates, in the first instance, to an agent for the treatment of hyperglycemia consisting of yeast cell walls as defined above, that is to say the yeast cell walls according to the invention. The treatment of hyperglycemia involves mainly the reduction of glycemia, that is to say of the blood glucose level.

This agent according to the invention may be useful in several cases of hyperglycemia, such as in particular the cases listed below:

(a) for the treatment of hyperglycemia in the case of type 2 diabetes (type 2 diabetes being called hereinafter "condition (a)");

(b) for the treatment of hyperglycemia in the case of gestational or pregnancy diabetes (gestational or pregnancy diabetes being called hereinafter "condition (b)");

(c) for the treatment of hyperglycemia in the case of prediabetes (prediabetes being called hereinafter "condition (c)");

(d) for the treatment of post-prandial hyperglycemia (the post-prandial state being called hereinafter "condition (d)").

The present invention also relates to an agent for the prevention of hyperglycemia, said agent consisting of yeast cell walls according to the invention. The prevention of hyperglycemia mainly involves keeping glycemia at levels below hyperglycemia.

Said agent may be in particular an agent for the prevention of hyperglycemia in the case of at least one of the conditions (a), (b), (c) or (d) as defined above.

The present invention also relates to an agent for the stabilization of glycemia, said agent consisting of yeast cell walls according to the invention. The stabilization of glycemia mainly involves keeping glycemia at levels below hyperglycemia and above hypoglycemia.

Said agent may be in particular an agent for the stabilization of glycemia in the case of at least one of the conditions (a), (b), (c) or (d).

The agent according to the invention, in its various embodiments, may be administered in various forms or presentations, alone or in combination with other ingredients, such as, for example, one or more other therapeutically active ingredients and/or one or more excipients.

Thus, the present invention relates to a preparation for the treatment of hyperglycemia which comprises yeast cell walls according to the invention, as defined above. Said preparation comprises, in other words, an agent according to the invention.

Said preparation according to the invention may be in particular a preparation for the treatment of hyperglycemia in the case of at least one of the conditions (a), (b), (c) or (d).

The present invention also relates to a preparation for the prevention of hyperglycemia which comprises yeast cell walls according to the invention.

Said preparation may be in particular a preparation for the prevention of hyperglycemia in the case of at least one of the conditions (a), (b), (c) or (d).

The present invention also relates to a preparation for the stabilization of glycemia which comprises yeast cell walls according to the invention.

Said preparation may be in particular a preparation for the stabilization of glycemia in the case of at least one of the conditions (a), (b), (c) or (d).

The preparation according to any one of the above embodiments is, generally a preparation for administration by the oral route.

The preparation may be provided in particular in the form of a tablet, a capsule, a pill, a powder, granules or a suspension.

The preparation according to the invention may also comprise one or more therapeutically active agents, and in particular one or more hypoglycemic agents. The preparation may thus comprise one or more vitamins, one or more dietary minerals, and the like.

The preparation may also comprise one or more pharmaceutically acceptable excipients.

The preparation according to the invention may be provided in particular in the form of a dose for ingestion corresponding to a quantity of yeast cell wall dry matter content according to the invention of less than 10 g, preferably from 1 to 8 g, preferably still from 1 to 7 g.

The present invention also relates to the use, in the preparation of a therapeutic composition or a medicament, of the yeast cell walls according to the invention, various embodiments of which are defined above.

The invention relates in particular to the use of these yeast cell walls in the production of one of the compositions according to the invention as defined above.

The present invention thus relates to the use of yeast cell walls according to the invention in the preparation of a therapeutic composition for the treatment of hyperglycemia.

The yeast cell walls according to the invention may be used in particular in the preparation of a therapeutic composition for the treatment of hyperglycemia in the case of at least one of the conditions (a), (b), (c) or (d).

The present invention also relates to the use of yeast cell walls according to the invention in the preparation of a therapeutic composition for the prevention of hyperglycemia.

The yeast cell walls according to the invention may be used in particular in the preparation of a therapeutic composition for the prevention of hyperglycemia in the case of at least one of the conditions (a), (b), (c) or (d).

The present invention also relates to the use of yeast cell walls according to the invention in the preparation of a therapeutic composition for the stabilization of glycemia.

The yeast cell walls according to the invention may be used in particular in the preparation of a therapeutic composition for the stabilization of glycemia in the case of at least one of the conditions (a), (b), (c) or (d).

The pharmaceutical composition is as a general rule a composition for administration by the oral route.

The pharmaceutical composition may be provided in particular in the form of a tablet, a capsule a pill, a powder, granules or a suspension.

The yeast cell walls according to the invention may be used in particular in the preparation of a pharmaceutical composition also comprising:
  one or more therapeutically active agents, in particular one or more hypoglycemic agents, and/or
  one or more vitamins, one or more dietary minerals, and the like.

The pharmaceutical composition may also comprise one or more pharmaceutically acceptable excipients.

The yeast cell walls according to the invention may be used in particular for the preparation of a therapeutic composition in the form of a dose for ingestion corresponding to a quantity of yeast cell wall dry matter content according to the invention of less than 10 g, preferably from 1 to 8 g, preferably still from 1 to 7 g.

The present invention additionally relates to a method for the treatment of hyperglycemia in a patient, comprising the administration to the patient of one agent according to the invention for the treatment of hyperglycemia or of a preparation according to the invention for the treatment of hyperglycemia.

The method for the treatment of hyperglycemia may be in particular a method for the treatment of hyperglycemia in the case of at least one of the conditions (a), (b), (c) or (d).

The present invention also relates to the use of an agent or of a preparation according to the invention in the treatment of hyperglycemia, in the prevention of hyperglycemia or in the stabilization of glycemia in a patient.

The present invention also relates to a method for the prevention of hyperglycemia in a patient, comprising the administration to the patient of an agent according to the invention for the prevention of hyperglycemia or of a preparation according to the invention for the prevention of hyperglycemia.

The method for the prevention of hyperglycemia may be in particular a method for the prevention of hyperglycemia in the case of at least one of the conditions (a), (b), (c) or (d).

The present invention also relates to a method for the stabilization of glycemia in a patient comprising the administration to the patient of an agent according to the invention for the stabilization of glycemia or of a preparation according to the invention for the stabilization of glycemia.

The method for the stabilization of glycemia may be in particular a method for the stabilization of glycemia in the case of at least one of the conditions (a), (b), (c) or (d).

The invention relates in particular to such a method in which the agent or the preparation is administered to the patient by the oral route.

The various methods according to the invention may comprise in particular the administration to the patient of the agent or of the preparation in a daily dose corresponding to 1 to 10 g, preferably from 2 to 8 g, preferably still from 3 to 6 g of yeast cell walls according to the invention, it being possible for said daily dose to be administered as a single dose or at a single moment of administration, such as for example during breakfast, or alternatively as several partial doses, that is to say spread out over the day.

The methods according to the invention may also comprise a step for checking glycemia in the patient after administration of the agent or of the preparation.

These methods may comprise in particular a step for measuring glycemia in the patient before the administration to the patient of the agent or of the preparation, and a step for checking glycemia in the patient after the administration to the patient of the agent or of the preparation.

EXAMPLES

A. Method for Producing Yeast Cell Walls According to the Invention.

An aqueous cream (that is to say a suspension of yeast cells in water) of *Saccharomyces cerevisiae*, having a dry matter content of between 12 and 18% by mass is subjected to hydrolysis with the aid of the endogenous enzymes of said yeast cells, optionally with addition of exogenous proteases to the yeast cells, such as for example papain. The hydrolysis is carried out at 50° C. for 24 hours, so as to solubilize at least 60% by mass of the dry matter content of the yeast cells.

Practically, in general, the autolyses or enzymatic hydrolyses according to the invention are carried out at between 45° C. and 55° C. for 18 to 36 hours, without the use of any enzyme capable of solubilizing the glucans or the mannoproteins.

The solubilized fraction is separated from the insoluble fraction by several successive steps of centrifugation and washing with water.

The insoluble fraction is dried on heated drums to a dry matter content of 95% by mass. The agglomerates formed are removed by sieving.

The yeast cell walls thus obtained have:
  a dry matter content of 95% by mass, an N×6.25 protein content of 20.2% by mass on a dry matter basis a total glucan and mannan content of 43% on a dry matter basis a glycogen content of 8% by mass on a dry matter basis.

B. Prevention and Treatment of Hyperglycemia by Means of a Preparation According to the Invention An 82-year-old disabled patient was diagnosed as suffering from type 2 diabetes.

Unable to participate in demanding physical exercises, the initial treatment was limited to a diet with a low content of fat and digestible sugars.

The effect obtained by virtue of this diet was limited. It was observed in particular that the patient's glycemia remained at a blood glucose content of 10.0 to 12.0 mmol/liter, knowing that a blood glucose content of between 4.0 and 7.0 mmol/liter, preferably of between 4.2 and 6.0 mmol/liter, was sought.

Subsequently, the abovementioned diet was supplemented by adding 3 to 4 g of yeast cell walls as described under point A above, to breakfast cereals.

Twelve hours after the first ingestion of said yeast cell walls, the patient's glycemia decreased to 6 mmol of blood glucose/liter.

On continuing the ingestion of 3 to 4 g of yeast cell walls per day during breakfast, the patient's glycemia was maintained for at least 4 months at between 4.5 and 6 mmol of blood glucose/liter.

No post-prandial hyperglycemia occurred during these 4 months, even after breaches of the prescribed diet, such as the consumption of chocolate.

No negative side effect was observed.

The invention claimed is:

1. A method for treating hyperglycemia in a subject with type 2 diabetes, comprising administering to said subject an agent consisting of cell walls of yeast of the species *Saccharomyces cerevisiae*, said yeast cell walls having:
   a total content of both glucans and mannans of at least 34.0% by mass on a dry matter basis, and
   a glycogen content of less than 10.0% by mass on a dry matter basis.

2. The method according to claim 1, wherein the yeast cell walls have a total content of both glucans and mannans of less than or equal to 70% by mass on a dry matter basis.

3. The method according to claim 1, wherein the yeast cell walls have a total content of both glucans and mannans of 55% to 70% by mass on a dry matter basis.

4. The method according to claim 1, wherein the yeast cell walls have a glycogen content of less than 1.0% by mass on a dry matter basis.

5. The method according to claim 1, wherein the yeast cell walls have a dry matter content greater than or equal to 90%.

6. A method for inhibiting hyperglycemia in a subject with type 2 diabetes, comprising administering to said subject an agent consisting of cell walls of yeast of the species *Saccharomyces cerevisiae*, said yeast cell walls having:
   a total content of both glucans and mannans of at least 34.0% by mass on a dry matter basis, and
   a glycogen content of less than 10.0% by mass on a dry matter basis.

7. The method according to claim 6, wherein the yeast cell walls have a total content of both glucans and mannans of less than or equal to 70% by mass on a dry matter basis.

8. The method according to claim 6, wherein the yeast cell walls have a total content of both glucans and mannans of 55% to 70% by mass on a dry matter basis.

9. The method according to claim 6, wherein the yeast cell walls have a glycogen content of less than 1.0% by mass on a dry matter basis.

10. The method according to claim 6, wherein the yeast cell walls have a dry matter content greater than or equal to 90%.

11. A method for stabilizing glycemia in a subject with type 2 diabetes, comprising administering to said subject an agent consisting of cell walls of yeast of the species *Saccharornyces cerevisiae*, said yeast cell walls having:
    a total content of both glucans and mannans of at least 34.0% by mass on a dry matter basis, and
    a glycogen content of less than 10.0% by mass on a dry matter basis.

12. The method according to claim 11, wherein the yeast cell walls have a total content of both glucans and mannans of less than or equal to 70% by mass on a dry matter basis.

13. The method according to claim 11, wherein the yeast cell walls have a total content of both glucans and mannans of 55% to 70% by mass on a dry matter basis.

14. The method according to claim 11, wherein the yeast cell walls have a glycogen content of less than 1.0% by mass on a dry matter basis.

15. The method according to claim 11, wherein the yeast cell walls have a dry matter content greater than or equal to 90%.

* * * * *

UNITED STATES PATENT AND TRADEMARK OFFICE
CERTIFICATE OF CORRECTION

PATENT NO. : 7,459,159 B2  
APPLICATION NO. : 10/567621  
DATED : December 2, 2008  
INVENTOR(S) : Lucien Lesaffre Page 1 of 1

It is certified that error appears in the above-identified patent and that said Letters Patent is hereby corrected as shown below:

Column 4, line 58, after "is" delete ",".  
Column 5, line 39, after "capsule" insert --,--.  
Column 8, line 27, "Saccharornyces" should read --Saccharomyces--.

Signed and Sealed this

Twelfth Day of January, 2010

David J. Kappos  
*Director of the United States Patent and Trademark Office*